United States Patent [19]

Bison et al.

[11] 3,941,814

[45] Mar. 2, 1976

[54] PROCESS FOR OBTAINING D(−)-AND L(+)-α-AZIDOPHENYLACETIC ACID

[75] Inventors: Gunter Bison, Troisdorf-Sieglar; Hans Schubel, Munich-Waldperlach; Gerhard Schmeling, Cologne, all of Germany

[73] Assignee: Dynamit Nobel Aktiengesellschaft, Germany

[22] Filed: July 29, 1974

[21] Appl. No.: 492,927

[30] Foreign Application Priority Data
July 28, 1973 Germany............................ 2338471

[52] U.S. Cl................................. 260/349; 260/399
[51] Int. Cl.²........................................ C07C 117/00
[58] Field of Search................................... 260/349

[56] References Cited
UNITED STATES PATENTS
3,755,373   8/1973   Rydh.................................. 260/349

*Primary Examiner*—Lewis Gotts
*Assistant Examiner*—Cary Owens
*Attorney, Agent, or Firm*—Craig & Antonelli

[57] ABSTRACT

L(+)- or D(−)-α-azidophenylacetic acid is produced by a process which involves the steps of reacting a water-soluble salt of DL-α-azidophenylacetic acid with a water-soluble salt of an optically active α-phenylethylamine in an aqueous medium, effecting crystallization of the resulting reaction product, that is, the diastereomeric salt, and splitting of the thus-obtained salt.

15 Claims, No Drawings

PROCESS FOR OBTAINING D(−)-AND L(+)-α-AZIDOPHENYLACETIC ACID

This invention relates to a process for obtaining D(−)- and L(+)-α-azidophenylacetic acid by reacting L(−)- or D(+)-α-phenyl-ethylamine with DL-α-azidophenylacetic acid, by crystallizing the thusformed diastereomeric salt, and by splitting or dissociating this salt.

D(−)-α-azidophenylacetic acid is employed as a starting material for the production of antibiotics such as α-aminobenzylpenicillin or α-azidobenzylpenicillin.

It has been known from British Pat. No. 960,665 that the free D(−)-α-azidophenylacetic acid can be obtained from the racemic form by reacting the racemic DL-α-azidophenylacetic acid in a lower alcohol with molar amounts of L-ephedrine, dehydroabietylamine, α-(2-naphthyl)-ethylamine, cinchonidine, cinchonine, quinidine, quinine, brucine, or morphine, by purifying the thus-isolated diastereomeric salt through repeated recrystallization, and by splitting the salt with a mineral acid.

It has furthermore been known that advantageous results can be obtained by conducting the splitting of the racemates of DL-α-azidophenylacetic acid by reaction with L(−)-α-phenylethylamine in organic diluents, such as benzene, ether, alcohols, or in water.

This process is disclosed in German Unexamined Laid-Open Application (DOS) No. 2,127,260. In this conventional process, equimolar amounts of L(−)-α-phenylethylamine and DL-α-azidophenyl-acetic acid are dissolved in solvents, and the solutions are reacted. In each case, it is disclosed that it is necessary to employ the free acid and the free base for the production of the diastereomeric salt.

Although the conventional racemate splitting of DL-α-azidophenylacetic acid with L(−)-α-phenylethylamine is advantageous as compared to the processes carried out with the aid of ephedrine and other alkaloids, it would be even more advantageous to be able to use, in the racemate splitting process, solutions of salts of DL-α-azidophenyl-acetic acid stemming directly from the synthesis of the salts to avoid the steps of obtaining the free acid from the salt. Furthermore, it would be advantageous if the purity of the thus-obtained D(−)-α-azidophenylacetic acid could be improved.

Consequently, the invention is based on the problem of making available a particularly economical process, which can be executed technically without flaws, for the production of D(−)- or L(+)-α-azidophenylacetic acid with the use of the antipodes of α-phenylethylamine, wherein solutions of the corresponding salts of the starting materials obtained directly during the preparation of the starting materials i.e., the salts of DL-α-azidophenylacetic acid, can be employed and the desired, optically active α-azidophenylacetic acids are produced in higher yields and with greater purity.

Therefore, this invention relates to a process for the production of D(−)- or L(+)-α-azidophenylacetic acid which comprises reacting a salt of DL-α-azidophenylacetic acid with a salt of an optically active α-phenylethylamine in an aqueous medium, crystallizing the reaction product, and splitting the thus-obtained crystallized salt.

In the process of this invention, the splitting base, L(−)- or D(+)-α-phenylethylamine, is utilized in the form of a water-soluble salt, especially as the hydrochloride, sulfate, or phosphate, during the reaction and during crystallization.

Salts of DL-α-azidophenylacetic acid suitable for purposes of the invention are also water-soluble salts, such as preferably the sodium, potassium, or ammonium salts.

The process of this invention has the extraordinary advantage that the formation of and the crystallization of the phenylethylamine salts of α-azidophenylacetic acid takes place with high selectivity directly in the mother liquor stemming from the preparation of the racemic α-azidophenylacetic acid. According to this process, high space-time yields and high productivity are attained. Moreover, by using the aqueous alkaline solution from the preceding preparation of synthesis stage, several process steps are avoided — precipitation, isolation, drying of the racemic acid. Also, the amount of wastewater is substantially reduced. The mode of operation of this invention also eliminates process operations required when working in organic and/or organic-aqueous solvents. The process of the present invention is particularly advantageous in the preparation and crystallization of the L(−)-α-phenylethylamine salt of D(−)-α-azidophenylacetic acid.

According to an especially advantageous embodiment of this invention, the salt of an optically active amine, e.g., L(−)-α-phenylethylamine is utilized in an amount substantially less than stoichiometric proportions, i.e. in from 0.1 to 0.5 mole and preferably in an amount of less than 0.5 mole per 1 mole of the salt of the racemic azidophenylacetic acid.

In case more than 0.5 mole of α-phenylethylamine per mole of DL-α-azidophenylacetic acid is employed in the reaction, the desired diastereomeric salt is no longer obtained in the pure form; the other antipode is concomitantly precipitated in minor amounts. Accordingly, the indicated upper molar ratio is critical.

The lower limit value for the amount of the optically active α-phenylethylamine employed is not critical, but should not be below 0.1 mole per 1 mole of the salt of the racemic azidophenylacetic acid, for economical reasons. In this embodiment of the process of the invention, the diastereomeric salts of L(−)- or D(+)-α-phenylethylamine with D(−)- or L(+)-α-azidophenylacetic acid are produced in a particularly pure form and with very good yields. Moreover, the splitting base, phenylethylamine, is most extensively exploited and need not be recovered. The antipode remaining in the aqueous solution, such as L(+)-α-azidophenylacetic acid, can then be directly racemized without separation or — if desired — can be isolated as a diastereomeric salt with D(+)-α-phenylethylamine according to the method of claim 1.

Theoretically, the formation of four diastereomeric salts is possible. L(−)-α-phenylethylamine forms a diastereomeric salt with D(−)-α-azidophenylacetic acid and with L(+)-α-azidophenylacetic acid. However, only the salt with D(−)-α-azidophenylacetic acid is insoluble and thus is precipitated.

Furthermore, a salt is possibly made up from D(+)-α-phenylethylamine and L(+)-α-azidophenylacetic acid or D(−)-α-azido-phenylacetic acid. Here again, only the salt formed with L(+)-α-azidophenylacetic acid is precipitated.

The process of this invention is explained with reference to the following examples:

EXAMPLE 1

Preparation of DL-α-Azidophenylacetic Acid

At 15 to 20°C., a solution of 430 g. of bromophenylacetic acid in 650 g. of trichloroethylene is added dropwise within 2 hours to a solution of 82.5 g. of caustic soda (i.e. sodium hydroxide) and 130 g. of sodium azide in 750 g. of water; the reaction mixture is agitated for 2 hours at 20°C.

At the end of the reaction, the resulting suspension has a pH of about 6, which is raised with 45% aqueous sodium hydroxide solution to a pH of 8. Thereafter, the lower (bottom) trichloroethylene phase is separated by decanting and the pH is lowered with the addition of concentrated sulfuric acid to 6 to 7. A sample is withdrawn from the reaction solution, and the content of α-azidophenylacetic acid is determined.

This analysis showed an 85% yield of α-azidophenylacetic acid, calculated on the basis of bromophenylacetic acid employed.

EXAMPLE 2

Under agitation, a solution of 96.7 g. of neutral L(−)-α-phenylethylamine sulfate in 560 g. of water is added to 1,120 g. of the aqueous mother liquor obtained according to Example 1 with an α-azidophenylacetic acid content of 247.2 g. at 20°C. as follows: 64 ml. is added dropwise within 20 minutes; the solution is inoculated with 0.3 g. of the L(−)-α-phenylethylamine salt of D(−)-α-azidophenylacetic acid with an optical purity of at least $[\alpha]_d 20 = -76.0°$ (c = 1 in absolute methanol); and the temperature of the reaction mixture is raised to 30° to 40°C. The residual solution is added dropwise under agitation within 3 hours. Already 20 minutes after the introduction of the aqueous L(−)-α-phenylethylamine sulfate solution, the crystallization commences. After the addition is terminated, the reaction mixture is cooled within 30 minutes to 20°C., and the diastereomeric salt is isolated by filtration, suction-filtering, or centrifugation, etc.

Yield: 151.0 g. (= 89.5% of theory, calculated on the basis of L(−)-α-phenylethylamine utilized) of the phenylethylamine salt of D(−)-α-azidophenylacetic acid.

Melting Point: 150°C.

$[\alpha]_D^{20} = -78°$ (c = 1 in absolute methanol).

EXAMPLE 3

Under agitation, 64.0 g. (0.37 mole) of L(−)-α-phenylethylamine sulfate, dissolved in 370 ml. of water, was added dropwise within 3 hours to a solution of 177 g. (1 mole) of DL(−)-α-azido-phenylacetic acid in 410 g. of 10% aqueous sodium hydroxide solution. After adding about 102 ml. of the phenylethylamine sulfate solution, the mixture was inoculated with a few crystals of D(−)-α-azidophenyl-acetic acid phenylethylamine salt (L $[\alpha]_D^{20} = -78°$ (c = 5 in absolute methanol). After completing the addition of phenylethylamine, the mixture was stirred for another 45 minutes; the thus-separated diastereomeric salt was vacuum-filtered and washed with 100 ml. of water.

Yield: 97 g. (= 87% theoretical, calculated on the basis of L(−)-α-phenylethylamine employed) of the phenylethylamine salt of D(−)-α-azidophenylacetic acid, having a rotation of $[\alpha]_D^{20} = -78°$ (c = 5 in absolute methanol).

By splitting the diestereomeric salt, 56 g. (= 84% theoretical) of D(−)-α-azidophenylacetic acid was obtained (based on α-phenylethylamine utilized); optical purity 98%.

As for the conditions under which the optically active salt of α-azidophenylacetic acid is precipitated with α-phenylethyl-amine, assuming water is used as the solvent, the concentration of the salt of DL-α-azidophenylacetic acid ranges between 0.05 and 0.75 grams per milliliter of water, preferably between 0.2 and 0.6 grams per milliliter of water. It will be appreciated that the diastereromeric salt is split according to generally conventional methods. Suitable for splitting purposes are, in principle, all mineral acids, hydrochloric acid is preferred. According to the present process, the D-form of the azidophenylacetic acid has been precipitated in the form of the ethylamine salt thereof, the L-form in the filtrate can be precipitated by adding to the filtrate a salt of D(+)-α-phenylethylamine.

The formation of the salt takes place without or preferably with agitation during addition of the phenylethylamine. The temperature can range between 10° and 80°C, a temperature range of between 25° and 60°C. is preferred. In general, the process is accomplished under normal pressure, in principle, it is also possible to operate at superatmospheric pressure. The reaction time ranges between 5 minutes and 5 hours.

While the novel principles of the invention have been described, it will be understood that various omissions, modifications and changes in these principles may be made by one skilled in the art without departing from the spirit and scope of the invention.

What is claimed is:

1. A process for obtaining L(+)- or D(−)-α-azidophenylacetic acid which comprises reacting a water-soluble salt of DL-α-azidophenylacetic acid with a water-soluble salt of optically active α-phenylethylamine in an aqueous medium containing solvent consisting essentially of water to produce a reaction product therein, crystallizing a diastereomeric salt of said acid and said amine from said reaction product and splitting the thus-obtained salt, said salt of optically active α-phenylethylamine being utilized in an amount of from 0.1 to 0.5 mole per mole of the salt of DL-α-azidophenylacetic acid.

2. The process according to claim 1, in which the salt of DL-α-azidophenylacetic acid is selected from the group consisting of the sodium, potassium, and ammonium salt.

3. The process according to claim 2, in which the salt of optically active α-phenylethylamine is a water-soluble inorganic acid salt of D(+) or L(−)-α-phenylethylamine.

4. The process according to claim 3, in which the inorganic acid salt is the hydrochloride, sulfate or phosphate of D(+)- or L(−)-α-phenylethylamine.

5. The process according to claim 1, in which the salt of DL-α-azidophenylacetic acid utilized is the sodium salt in a solution obtained during the preparation of the acid by reaction of α-bromophenyl-acetic acid and sodium azide.

6. The process according to claim 1, in which the salt of optically active α-phenylethylamine is D(+)- or L(−)-α-phenylethylamine.

7. The process according to claim 6, in which the salt of D(+)- or L(−)-α-phenylethylamine is utilized in an amount of 0.5 mole per mole of the salt of DL-α-azidophenylacetic acid.

8. The process according to claim 1, in which the reaction of the water-soluble salt of DL-α-azidophenylacetic acid with the water-soluble salt of optically active α-phenylethylamine is conducted at a temperature of from about 10° to 100°C. for from 15 to 300 minutes.

9. The process according to claim 1, in which the concentration of the water-soluble salt of DL-α-azidophenylacetic acid in the aqueous medium is from 0.05 to 0.75 g. per milliliter of water.

10. The process according to claim 1, wherein crystallization of the salt is promoted by incremental addition of a water-soluble salt of the α-phenylethylamine, together with the inoculation of an optically active α-phenylethylamine salt of one of the antipodes of α-azidophenylacetic acid and an increase in the temperature of the reactants, followed by gradual cooling.

11. The process according to claim 10, wherein the inoculation is effected at a temperature of from 10° to 40°C. the temperature of the reactants is raised by an increase of between 5° and 30°C. and preferably the increase in temperature ranges between 10° and 20°C.

12. The process of claim 1, further comprising isolating the diastereomeric salt from said reaction product and then splitting said diastereomeric salt by treatment with an inorganic acid.

13. The process according to claim 1, in which the reaction of the water-soluble salt of DL-α-azidophenylacetic acid with the water-soluble salt of optically active α-phenylethylamine is conducted at a temperature of from about 20° to 60°C. for from 15 to 300 minutes.

14. The process according to claim 1, in which a salt of L(−)-α-phenylethylamine is reacted with a salt of DL-α-azidophenylacetic acid to provide a reaction product containing the L(−)-α-phenylethylamine salt of D(−)-α-azidophenylacetic acid and D(−)-α-azidophenylacetic acid is obtained by splitting of said thus-obtained salt.

15. The process according to claim 1, in which a water-soluble salt of D(+)-α-phenylethylamine is reacted with the water-soluble salt of DL-α-azidophenylacetic acid to produce a reaction product containing the D(+)-α-phenylethylamine salt of L(+)-α-azidophenylacetic acid and L(+)-α-azidophenylacetic acid is split from said thus-obtained salt.

* * * * *